United States Patent [19]

Maitz et al.

[11] Patent Number: 5,062,835
[45] Date of Patent: * Nov. 5, 1991

[54] ASPIRATOR DEVICE FOR BODY FLUIDS

[76] Inventors: Carlos A. Maitz, 16451 Dapple Gray Ct., Chesterfield, Mo. 63017; George M. Hauser, 29 Chieftan Dr., St. Louis, Mo. 63146

[*] Notice: The portion of the term of this patent subsequent to May 1, 2007 has been disclaimed.

[21] Appl. No.: 444,316

[22] Filed: Dec. 1, 1989

Related U.S. Application Data

[63] Continuation of Ser. No. 144,375, Jan. 15, 1988, Pat. No. 4,921,488.

[51] Int. Cl.$^5$ .............................................. A61M 5/00
[52] U.S. Cl. .................................. 604/153; 604/181; 604/247; 604/319
[58] Field of Search .................... 604/48–51, 604/54, 73, 131, 133, 151, 181, 183, 212, 213, 217, 247, 316–319; 128/201.25, 201.28, 205.19, 206.22, 207.14, 207.16

[56] References Cited

U.S. PATENT DOCUMENTS

| | | | |
|---|---|---|---|
| 660,212 | 10/1900 | Ertsman | 604/181 |
| 3,018,779 | 1/1962 | Tyler et al. | 604/181 |
| 3,542,026 | 11/1970 | Bledsoe | 128/201.28 |
| 4,073,294 | 2/1978 | Stanley et al. | 604/217 |
| 4,275,724 | 6/1981 | Blerstock | 604/281 |
| 4,319,570 | 3/1988 | Grane | 604/317 |

FOREIGN PATENT DOCUMENTS 3442192  1/1986  Fed. Rep. of Germany ...... 604/319

Primary Examiner—Stephen C. Pellegrino
Attorney, Agent, or Firm—Polster, Polster and Lucchesi

[57] ABSTRACT

An aspirator device for removing body fluids is disclosed as having a fluid collector with an air-type chamber that communicates with a first sealed passageway in an elongated flexible tube to be inserted in a body cavity for fluid communication with body fluids, and a second sealed passageway which connects the air tight chamber with a manually operable vacuum device or squeeze bulb. The manually operable vacuum means or squeeze bulb is operatively associated with first and second one-way valve which open in the same direction, the first valve establishing a vacuum in the first and second sealed passageways for remvoing and depositing harmful body fluids in the fluid collector, and the second valve means not only working to establish the vacuum, but also serving as an overflow valve for fluids overflowing the fluid collector. The manually operable vacuum device or squeeze bulb is also supported in a relatively stable and rigid position relative to the fluid collector to facilitate one-handed gripping and operation thereof by a user.

3 Claims, 2 Drawing Sheets

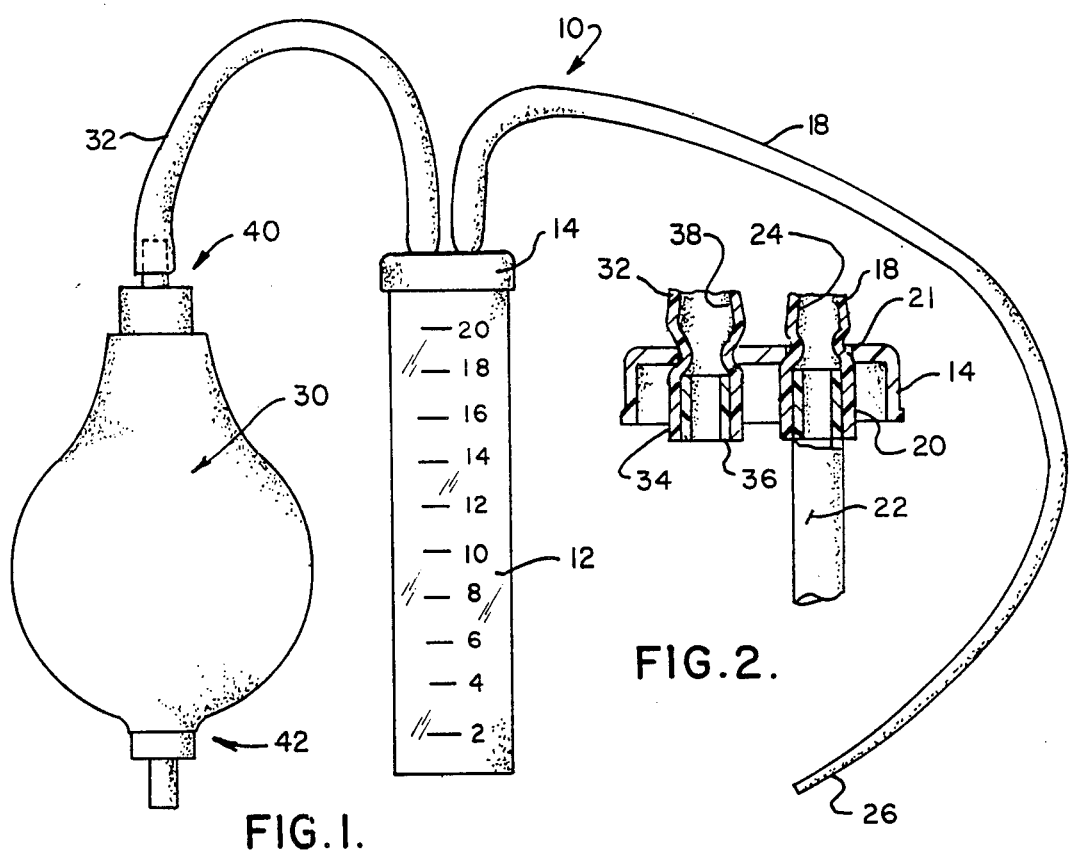
FIG. 1.
FIG. 2.
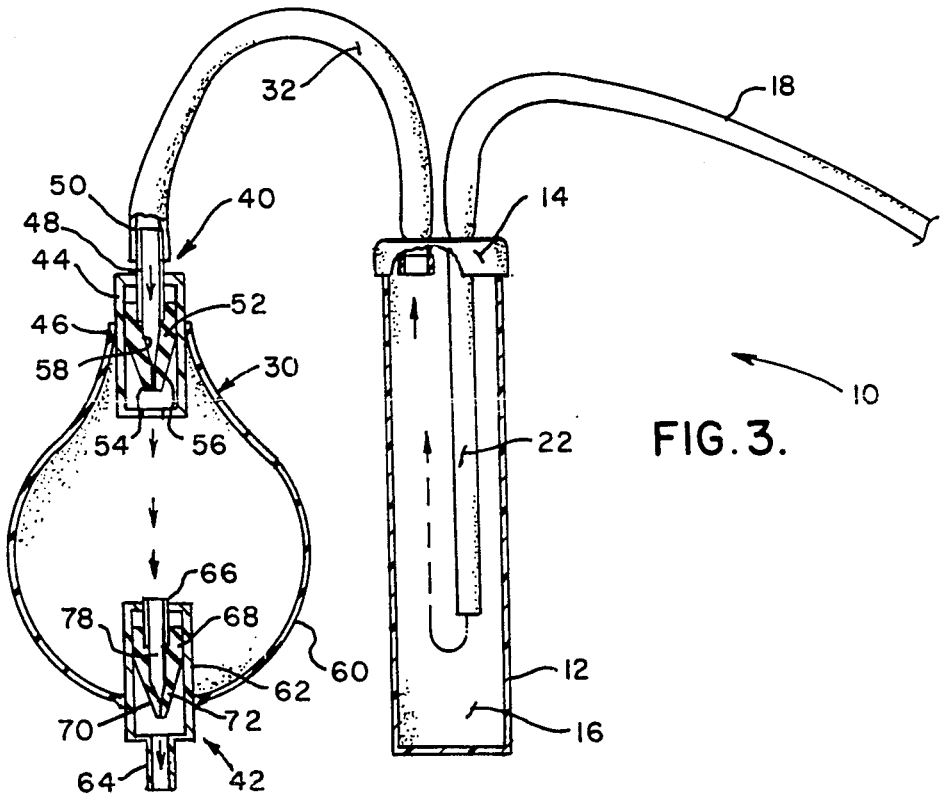
FIG. 3.

ASPIRATOR DEVICE FOR BODY FLUIDS

This is a continuation of copending application Ser. No. 144,375, filed on Jan. 15, 1988, now U.S. Pat. No. 4,921,488.

BACKGROUND OF THE INVENTION

This invention relates to aspirator devices for removing harmful body fluids, and more particularly, relates to aspirator devices which can remove meconium or mucus fluids from a baby's stomach and lungs during delivery, as well as remove other potentially harmful body fluids.

It is well known to remove meconium fluids from the stomach and lungs of a baby during the delivery process. Even before the baby leaves the mother's birth canal, an obstetrician cleans out meconium fluid from the stomach of the baby being delivered. Sometimes, pediatricians also clean out the meconium fluid from the lungs of a baby during or shortly after delivery. It has been found most desirable to remove the meconium fluids during delivery since the birth canal compresses the stomach and lungs to assist in "pumping out" the meconium fluid.

One typical aspirator device which is used for this purpose is known as the "De Lee Suction Catheter with Mucus Trap" manufactured by the Sherwood Medical Company of St. Louis, Missouri. Such devices include a mucus trap or collector which is air tight and sealed to a first flexible plastic tube that extends into the mouth of a baby and a second flexible plastic tube, also air tight, sealed to the collector. The second flexible tube has at its free end a small mouth piece which the doctor inserts in his mouth to draw vacuum through the system to deposit harmful body fluids, i.e., the meconium fluid, into the collector.

It is also well known that such aforementioned devices sometimes permit fluids which overflow the collector to be sucked into the mouth of the doctor. While this does not repeatedly occur, every obstetrician and pediatrician has faced this unpleasant situation. If the baby or mother is infected with AIDS or other highly contagious disease it is quite apparent that for this situation to occur even once is one too many times. In an effort to solve this problem, the aforementioned devices have been "hooked up" to the hospital suction systems; however, not only does this require long lengths of connected tubing, the entire hospital vacuum suction system may become contaminated.

There are examples of other prior art devices which use manually operable vacuum means or squeeze bulbs to remove fluids from a container or body including U.S. Pat. No. 555,588; 659,470; 2,264,099; 2,511,469; 3,683,929 and 3,848,603. While these aforementioned devices operate for the variety of purposes shown in such patents and some have even suggested the use of squeeze bulbs with one or more valves to limit return flow of fluid, the fact is that as of the filing date of this application, the highly developed medical community, including medical supply companies, in the United States, continue to use the doctor's mouth as the means of suction to operate meconium aspirator devices, for removing meconium fluid from babies. While the doctor's mouth suction frees up the doctor's hands for use, the potential risk of exposure to highly contagious diseases does not justify the continued use of such systems.

It is thus apparent that the current devices and/or prior art patents have not fully considered the doctor's needs which include removal of meconium fluid and measurement of the quantity of meconium fluid received, while also permitting excess overflowing fluids to be removed from the system, without risk to the doctor. Further, such current devices and prior art patents have not fully considered the coordinated use of the doctor's hands, in removing meconium fluid, while not inhibiting the doctor in the use of his hands during the delivery process.

SUMMARY OF THE INVENTION

Accordingly, among the objects and the advantages of the present invention include:

The provision of an aspirator device which removes harmful body fluids without unnecessary health exposure to doctors using the device;

The provision of a self-contained aspirator device which facilitates the removal of harmful body fluids through a manually operable vacuum means or squeeze bulb;

The provision of an aspirator device of the type aforementioned which also permits overflowing fluids to be removed from the aspirator device without unnecessary health exposure;

The provision of an aspirator device of the type aforementioned which is positioned and supported in a relatively rigid and stable location relative to the other components of the device to facilitate one-handed operation and use; and The provision of an aspirator device of the type aforementioned which: can be readily adapted into existing systems; is simple and easy to use; is relatively inexpensive in view of the results provided; is disposable; and is otherwise well adapted for the purposes intended.

Briefly stated, the aspirator device of the present invention for removing harmful body fluids is provided with a fluid collector having an air tight chamber for receiving harmful body fluids. An elongated flexible tube includes a first sealed passageway which communicates with the air tight chamber and also has a free end adapted to be inserted into a body cavity for fluid communication with body fluids. A manually operable vacuum means, preferably in the form of a squeeze bulb, is connected to the collector via a second sealed passageway which communicates with the air tight chamber of the collector. The manually operable vacuum means, or squeeze bulb is operatively associated with first and second valve means which open in the same direction. The first one-way valve means is operatively connected relative to the manually operable vacuum means and second sealed passageway to permit air to be withdrawn in one direction through the first sealed passageway, air tight chamber and second sealed passageway upon activation of the manually operable vacuum means to establish a vacuum through the passageways to remove harmful body fluids for deposit in the collector. A second one-way valve means is operatively connected to the manually operable vacuum means to allow air to be withdrawn therethrough as well as permit fluids overflowing the collector to be drawn past the first one-way valve means for discharge through the second one-way valve means and removal of the overflowing fluids by operation of the manually operable vacuum means. Preferably also, the configuration, arrangement and position of the manually operable vacuum means, relative to the other components, facilitates one-handed gripping and operation of the aspirator device by a user.

BRIEF DESCRIPTION OF THE DRAWINGS

FIG. 1 is a front elevational view of the aspirator device of the present invention including a fluid collector and manually operable vacuum means or squeeze bulb;

FIG. 2 is an enlarged fragmentary vertical sectional view illustrating one manner in which the flexible tubing of the aspirator device is connected to the fluid collector;

FIG. 3 is a fragmentary front elevational view, partly in section, illustrating the manner in which the aspirator device establishes a vacuum to withdraw body fluids, as well as permitting overflowing fluids to be removed from the device;

DESCRIPTION OF THE PREFERRED EMBODIMENT

Figure 4:
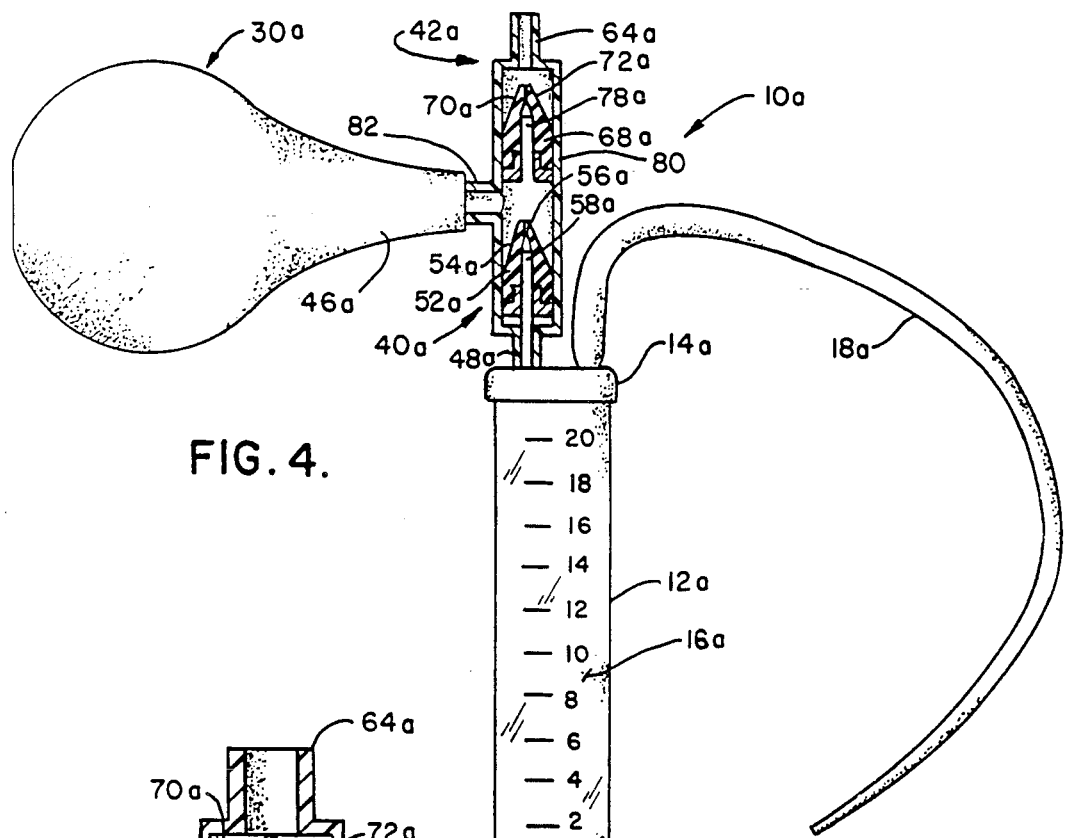
FIG. 4 is a front elevational view, partly in section, illustrating another embodiment of the aspirator device of the present invention.

In the description that is to follow, it is to be understood that the aspirator device for body fluids has been principally developed for use in removing meconium fluid from a baby during or shortly after delivery. As previously explained, the preferred time to do this is while the baby is still in the birth canal since the mother's contractions can aid in "pumping out" the harmful meconium fluid. In the normal delivery, the amount of fluid removed is deposited in a fluid collector, measured and recorded in the delivery notes of the doctor. Where excess stress produces an abnormal amount of meconium fluid, sometimes the fluid collector overflows, and this problem must be dealt with without risk to the patient, child, doctor or other occupants in the delivery room. At the same time, the system must be designed to facilitate coordinated use of the doctor's hands during the delivery process. Fortunately, the present invention provides a very practical and effective system which meets all of the required demands of the doctor, patient, baby and other delivery room occupants. This system may also be used for removing other harmful body fluids, as may be appropriate.

The term "fluid" or "fluids" as used herein includes gases, liquids and/or particulate solids or any combination thereof.

Referring now to the drawings, it will be seen that the aspirator device 10 for removing harmful body fluids includes a fluid collector 12 and a cap or cover 14 covering the open upper end of the fluid collector 12 to define an air-tight chamber 16 for receiving the harmful body fluids. The fluid collector serves as a specimen container and is graduated to provide measurement in fluid cc's for recording in the doctor's delivery notes. An elongated flexible tube 18 is connected to the fluid collector 12 and its associated cap or cover 14 as shown in FIG. 2 of the drawings. There, it will be seen that one end 20 of the flexible tube 18 is inserted into a corresponding opening 21 of the cap or cover 14 to permit engagement and enlargement of the end 20 through the insertion of the rigid tube 22 into the tubular open end 20 of the flexible tube 18. As is illustrated in FIG. 2, the tubular end 20 of the flexible tube is deformed to lock the tubular end 20 relative to the cap or cover 14. In addition, the tubular end 20 engages the marginal edge or periphery surrounding the opening 21 and the cap or cover 14 to provide and air-tight seal therewith. In this way, a first sealed passageway 24 within the flexible tubing 18 communicates through the rigid tube 22 within the air-tight chamber of the fluid collector 12 and associated cap or cover 14. The flexible tube 18 contains a crimp to retain tube 18 in position relative to cap 14 and opening 21. Flexible extraction tube 18 is also preferably tapered from the end connected to the fluid collector 12 to the free end 26 to facilitate insertion within the baby's mouth, stomach, and lungs for removing meconium fluid. In an alternate design the extraction tube is relatively firm over a section of its length in nearest proximity to the fluid collector 12 including the right-angle elbow 10 and then becomes progressively tapered and more flexible throughout the remainder of its length to facilitate aiming and manipulating the tapered end into body passageways.

Existing commercial prior art devices utilize the aforementioned components together with a second flexible tube which is in air-tight fluid communication with the fluid collector. The second flexible tube utilizes a mouthpiece at its free end to enable a doctor to use the doctor's mouth in creating a vacuum throughout the system to draw the meconium fluid into the fluid collector. For the reasons previously discussed, this known system creates an unnecessary potential risk and exposure of the doctor to harmful body fluids which might further contain a highly contagious disease.

Therefore, in accordance with an important feature of the present invention, the aspirator device includes a manually operable vacuum means or squeeze bulb 30 which is connected to the fluid collector 12 through the elbow or reversely bent tube section 32 which extends between the squeeze bulb 30 and the fluid collector 12. As shown in FIG. 2, one end 34 of the formed elbow or tube section 32 has a rigid locking ring 36 inserted within the tubular end 34 for locking the formed tube section 32 relative to the cap or cover 14, and for also creating an air-tight seal therewith. Thus, a second sealed passageway 38 extends within the elbow or reversely bent tube section 32 which communicates between the fluid collector and the squeeze bulb 30.

A second method of attaching tubes 18 and 32 to cap 14 deletes the rigid tube 22 and locking ring 36. The end 20 of flexible tube 18 can be extended by an amount equal to the length of rigid tube 22. Under the second method, the tubes 18 and 32 are held in position relative to the cap 14 by the crimped section only in tubes 18 and 32 as shown in the drawings.

The squeeze bulb 30 includes normally closed one-way valve means 40, 42 associated specifically therewith, the first one-way valve means 40 includes a cylindrically shaped housing 44 which is received in the gooseneck end 46 of the squeeze bulb 30 as shown in FIG. 3. Extending upwardly from the cylindrically shaped housing 44 is a rigid tubular section 48 which is received within the outer free end 50 of the elbow or reversely bent tube section 32. The rigid tube section 48 also communicates and extends within the interior of the cylindrically shaped housing 44 for cooperation with the one-way flapper valve 52 which opens and closes in response to squeezing and expansion of the squeeze bulb 30. The flapper valve 52 is formed from a soft resilient plastic material. Under normal conditions of zero differential pressure between the ends of valve 52, the valve 52 is closed to the flow of air or body fluids. The differential pressure between the ends of the valve 52 is derived by squeezing the bulb 30 causing the valve to close tighter and thereby prevent flow through the valve. Releasing the previously squeezed bulb imposes a reverse differential pressure which causes the resilient valve walls 54, 56 to part and thereby permit air or body fluids to be drawn through flexible tubes 18 into collector 12, and then through valve 52 and finally into bulb 30. Similarly, the second one-way valve means 42 is mounted in the bulbous end portion 60 of the squeeze bulb 30 and includes a cylindrical housing 62 extending through a corresponding opening in the bulbous end portion 60 of the squeeze bulb 30. The housing 62 includes a rigid tube section 64 which extends outside of the squeeze bulb 30 as illustrated in FIG. 3. At the opposite end of the cylindrical housing 62 is a second tubular section 66 which extends interiorly of the cylindrical housing 62 and communicates with the flapper valve 68. The flapper valve 68 is identical to flapper valve 52 and includes the normally closed resilient valve walls 70, 72 which are opened in response to a differential fluid pressure caused by squeezing the bulb 30 to expose the opening 78 in the flapper valve 68 and thereby expel air and body fluids from the system.

Thus, upon squeezing the squeeze bulb 30, air within the squeeze bulb 30 will be forced out of the second one-way valve means 42 through the opening in the tube section 66 and the opening 78 in the flapper valve 68, causing the resilient valve walls 70, 72 to move apart from one another to allow air and body fluid (if any) to be evacuated through the second one-way valve means 42. Upon release and subsequent expansion of the squeeze bulb 30, the negative differential air pressure within the squeeze bulb 30 causes the flapper walls 54, 56 of the one-way valve means 40 to open to expose the opening 58 of the flapper valve 52 to draw air through the second passageway 38, the fluid collector 12 and through the first passageway 24, to remove harmful body fluids that are in fluid communication with the free end 26 of the flexible tube 18. Arrows are shown in FIG. 3 of the drawings to represent movement of air in the aspirator device 10 upon squeezing and subsequent expansion of the squeeze bulb 30. Any fluid that is drawn up into the first passageway 24 will be deposited within the fluid collector 12 to permit removal of any harmful body fluids. In a normal delivery, the doctor can measure from two to twenty cc's of meconium fluid that are drawn into and received within the fluid collector 12.

Sometimes however, the meconium fluid drawn into the system exceeds the capacity of the fluid collector 12. The aspirator device 10 will allow any such excess fluid to be removed from the system through the first and second one-way valve means 40, 42. Specifically, liquid that is drawn up into the second passageway 38 of the elbow or reversely bent tube section 32 is drawn into the first one-way valve means 40 and into the opening 58 of the flapper valve 52 causing the flapper walls 54, 56 to be spread apart and allowing the liquid to enter into the squeeze bulb 30. Subsequent squeezing and expansion of the squeeze bulb 30 also causes the liquid to enter into the second one-way valve 42 and into the opening 78 of the flapper valve 68, causing the flapper walls 70, 72 to be spread apart and allowing the liquid to be evacuated out through the rigid tubular section 64.

In addition to removing excess body fluids from the aspirator 10, it will be noted that the squeeze bulb 30 is positioned relative to the fluid collector 12 to enable the doctor to grip one or both of the same to facilitate one-handed operation thereof. As will be appreciated, the elbow or reversely bent tube section 32 is a formed tubular plastic member which supports the squeeze bulb 30 in a relatively rigid and stable position relative to the fluid collector 12 as shown in FIG. 2-3 of the drawings. The elbow or reversely bent tube section 32 need not be entirely rigid and can accommodate some flexibility as a result of the connection and support of the free end 34 of the tube section 32 relative to the cap or cover 14, as has been previously described. The arrangement, configuration and positioning of the squeeze bulb 30 relative to the fluid collector 12 is thus able to facilitate one-handed gripping and operation of the aspirator device 10 by a user. A doctor is thus able to use one hand to operate the aspirator device 10, while having the other hand free to assist in the delivery of the baby. Since the aspirator device 10 is used for only a short period during the delivery process, the use of one hand to operate the aspirator device 10 does not restrict the doctor in the use of both hands during most of the delivery process. An assistant, if available, can also utilize the apparatus during the delivery.

Figures 5, 6:
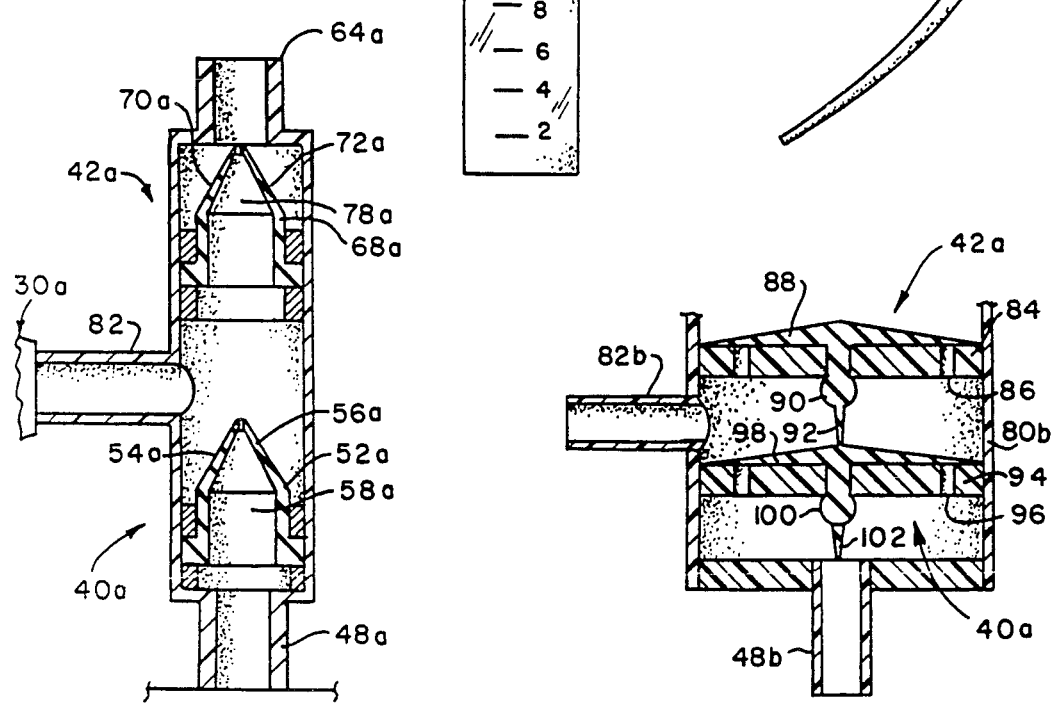
FIG. 5 is an enlarged vertical sectional view illustrating the construction and arrangement of the one-way valves in the valve enclosure of the FIG. 4 embodiment.
FIG. 6 is also an enlarged vertical sectional view of another form of one-way valve means contained within its own valve enclosure.

Reference is now made to FIGS. 4-6 of the drawings for a description of several additional embodiments of the present invention. In referring to these embodiments, similar reference numerals will be used to designate like parts with the addition of alphabetical suffixes to differentiate between the different embodiments.

In the FIGS. 4-5 embodiment, it will be noted that there is no reversely bent tube section 32, but instead there is a double-sized integral housing 80 in which the first and second normally closed valve means 40a, 42a operate. The enclosure or housing 80 has a lower tubular section 48a which is directly interconnected relative to cap or cover 14a for air-tight fluid sealed communication with the interior air-tight chamber 16a of the fluid collector 12a. At the upper end of the housing 80 is an integral upstanding tube section 64a which communicates with the atmosphere. An integral and transversely extending mid-sized positioned tube section 82 extends from the housing 80 and is received within the gooseneck portion 46a of the squeeze bulb 30a. In operation, the aspirator device 10a of the FIGS. 4-5 embodiment operates in a similar manner to the aspirator 10 of the FIGS. 1-3 embodiment. Thus, as the squeeze bulb 30a is pressed, air is exhausted through the normally closed one-way valve means 42a, and upon subsequent expansion of the squeeze bulb 30a, the normally closed one-way valve means 40a as the flapper walls 54a, 56a opened to expose the opening 58a which communicates with the air-tight chamber 16a of the aspirator device 10a, to establish the vacuum throughout the system, and thereby draw fluid into the fluid collector 12a. In the event of any excess of fluid in the fluid collector, the fluid is directed upwardly past the flapper valve 52a and into the hollow chamber squeeze bulb 30a. Continued compression and expansion of the squeeze bulb 30a causes the excess liquid to be expelled or discharged through the one-way valve means 42a through the upstanding tubular projection 64a to the atmosphere. The housing 80 provides a substantially stable and rigid position of the squeeze bulb 30a in close proximity to the fluid collector 12a, for lifting and operation of the aspirator device 10a during removal of harmful body fluids.

The embodiment shown in FIG. 6 is similar to the FIGS. 4-5 embodiment but discloses a different valve arrangement. This embodiment includes an outer housing 80b into which the valves 40a, 42a are mounted and a transverse tube section 82b which is available for cooperative engagement with a squeeze bulb. In addition, the housing 80b includes a downwardly extending tubular section 48b which is available for insertion into the cap adaptor device. The cap adaptor device, for example, may consist of a short section of flexible tubing 32 extending outwardly from the cap as shown in FIG. 2. Assembly is accomplished by inserting tubular section 48a of FIG. 5 or 48b of FIG. 6 into this short section of flexible tubing (not shown) extending outwardly from the cap 14. The valves 40a, 42a are constructed differently in the FIG. 6 embodiment. Referring first to the upper valve 42a, the valve arrangement includes a rigid transverse plate 84 having a plurality of openings 86 therein and a resilient disk-shaped valve element 88 which normally closes the openings 86. The resilient disk-shaped valve cover 88 is held in place in abutting relationship with the plate 84 on one side thereof as a result of the enlarged head 90 integrally associated therewith which engages the opposite side of the plate 84, as shown in FIG. 6. A integral depending tip 92 is used during assembly and should not contact the corresponding disk of the lower element. The valve 40a includes a plate 94 having a plurality of openings 96 formed therein which are also covered by the disk-shaped valve element 98 which normally closes the openings 96. The enlarged head 100 maintains the disk-shaped element 98 in the position shown in FIG. 6 of the drawings, and a depending integral tip 102 is used during assembly and extends downwardly therefrom as shown. In operation, when an associated squeeze bulb is compressed, air is exhausted outwardly through the opening 86 and the disk-shaped element 88 is deformed along its outer thinner periphery. Upon subsequent expansion of the squeeze bulb, the differential air pressure between the valves 40a, 42a causes the outer periphery of the disk-shaped element 98 to be distorted allowing exposure of the openings 96 in the valve 40a to establish a vacuum throughout the aspirator device in this embodiment. Fluid would then flow into a corresponding fluid collector, until excess fluid if any, is encountered. Thereupon, the excess fluid will be drawn through the opening 96 of the one-way valve 40a into the chamber of the associated squeeze ball, and upon subsequent compression and expansion, the excess fluid would be discharged through the openings 86 in the one-way valve means 42a.

In view of the above disclosures, it will now be apparent that the aforenoted objectives and advantages of the present invention have been achieved In actual use in the delivery room, devices made in accordance with the present invention have been found to be extremely useful and convenient for both the doctor and the doctor's assistant. Furthermore, such devices have performed well and have met all the necessary criteria initially contemplated in the development of this invention.

While the invention has been described with respect to embodiments, it will be understood that various modifications and variations will occur to those skilled in the art from the foregoing detailed description and the accompanying drawings. Such modifications and variations are intended to fall within the scope of the appended claims.

Having thus described the invention, what is claimed and desired to be secured by Letters Patent is:

1. A meconium aspirator device for removing body fluids comprising a fluid collector having an air-tight chamber for receiving body fluids, an elongated flexible tube securely connected to said collector and including a first sealed passageway communicating with said air-tight chamber, said elongated flexible tube having a free end adapted to be inserted into a body cavity for fluid communication with body fluids, a squeeze bulb securely connected to said collector and associated with a second sealed passageway communicating with the air-tight chamber of said collector, said squeeze bulb being operatively associated with first and second one-way valve means which open in the same direction, said first and second valve means comprising normally closed valve means which open and close in response to squeezing and expansion of said squeeze bulb, said first one-way valve means being operatively connected relative to said second sealed passageway to permit air to be withdrawn in one direction through the first sealed passageway, air-tight chamber and second sealed passageway upon compression and release of said squeeze bulb for establishing a vacuum through said passageways to remove body fluids for deposit of liquid content in said collector, said second one-way valve means being operatively connected to said squeeze bulb to allow gas and vapor to be expelled therethrough to atmosphere, and said squeeze bulb being operatively associated relative to the other components of said aspirator device to facilitate one-handed gripping, lifting and operation of said aspirator device by said squeeze bulb alone.

2. A meconium aspirator device for removing body fluids comprising a fluid collector having an air-tight chamber for receiving body fluids, an elongated flexible tube connected to said collector and including a first sealed passageway communicating with said air-tight chamber, said elongated flexible tube having a freeze end adapted to be inserted into a body cavity for fluid communication with body fluids, a squeeze bulb connected to said collector and associated with a second sealed passageway communicating with the air-tight chamber of said collector, said squeeze bulb being connected to said second sealed passageway at a location remote from said collector and including first and second one-way valve means which open in the same direction, said first one-way valve means being connected to said second sealed passageway to permit air to be withdrawn in one direction through the first sealed passageway, air-tight chamber and second sealed passageway upon compression and release of said squeeze bulb for establishing a vacuum through said passageways to remove body fluids for deposit of liquid content in said collector, and said second one-way valve means being connected to said squeeze bulb to allow gas and vapor to be expelled therethrough to atmosphere as well as permit liquids overflowing the collector to be drawn through the first one-way valve means for discharge through said second one-way valve means and removal of gas, vapor and overflowing fluids from said squeeze bulb at a location remote from said collector and said first sealed passageway.

3. A meconium aspirator device for removing body fluids comprising a fluid collector having an air-tight chamber for receiving body fluids, an elongated flexible tube connected to said collector and including a first sealed passageway communicating with said air-tight chamber, said elongated flexible tube having a free end adapted to be inserted into a body cavity for fluid communication with body fluids, a squeeze bulb connected to said collector and associated with a second sealed passageway communicating with the air-tight chamber of said collector, said squeeze bulb being connected to said second sealed passageway at a location remote from said collector and including first and second one-way valve means which open in the same direction, said first one-way valve means being connected relative to said second sealed passageway to permit air to be withdrawn in one direction through the first sealed passageway, air-tight chamber and second sealed passageway upon compression and release of said squeeze bulb for establishing a vacuum through said passageways to remove body fluids for deposit of liquid content in said collector, and said second one-way valve means being connected to said squeeze bulb to allow gas and vapor to be expelled through the squeeze bulb and second one-way valve means to atmosphere.

* * * * *